(12) United States Patent
Hubbard (10) Patent No.: US 10,070,957 B2
(45) Date of Patent: Sep. 11, 2018

(54) MEMBRANE ENCAPSULATED JOINT IMPLANT SEALED UNDER VACUUM

(71) Applicant: Dallin Andrew Hubbard, Salt Lake City, UT (US)

(72) Inventor: Dallin Andrew Hubbard, Salt Lake City, UT (US)

(*) Notice: Subject to any disclaimer, the term of this patent is extended or adjusted under 35 U.S.C. 154(b) by 0 days.

(21) Appl. No.: 15/478,114

(22) Filed: Apr. 3, 2017

(65) Prior Publication Data

US 2017/0281351 A1 Oct. 5, 2017

Related U.S. Application Data

(60) Provisional application No. 62/317,910, filed on Apr. 4, 2016.

(51) Int. Cl.
| | |
|---|---|
| *A61F 2/32* | (2006.01) |
| *A61F 2/30* | (2006.01) |
| *A61F 2/40* | (2006.01) |
| *A61F 2/36* | (2006.01) |
| *A61F 2/34* | (2006.01) |
| *A61F 2/42* | (2006.01) |
| *A61F 2/44* | (2006.01) |

(52) U.S. Cl.
CPC ......... *A61F 2/30* (2013.01); *A61F 2/34* (2013.01); *A61F 2/3662* (2013.01); *A61F 2/4014* (2013.01); *A61F 2/4081* (2013.01); *A61F 2/42* (2013.01); *A61F 2/44* (2013.01); *A61F 2002/30518* (2013.01); *A61F 2002/30591* (2013.01); *A61F 2002/30649* (2013.01); *A61F 2002/30673* (2013.01); *A61F 2002/345* (2013.01)

(58) Field of Classification Search
CPC .... A61F 2/344014; A61F 2/4081; A61F 2/42; A61F 2/44; A61F 2002/30591; A61F 2002/30673
See application file for complete search history.

(56) References Cited

U.S. PATENT DOCUMENTS

| | | | |
|---|---|---|---|
| 6,761,741 B2* | 7/2004 | Iesaka | A61F 2/30742 623/22.11 |
| 2011/0153025 A1* | 6/2011 | McMinn | A61F 2/30771 623/20.32 |

* cited by examiner

*Primary Examiner* — Brian Dukert
(74) *Attorney, Agent, or Firm* — Kunzler, PC (57) ABSTRACT

For a membrane encapsulated joint implant sealed under vacuum, a joint implant includes an outer cup, an inner cup, a joint head, a joint membrane, a lubricant, and an implant stem. The outer cup attached at a proximal bone. The nests within the outer cup and receives a joint head, the inner cup comprising an inner cup rim. The joint head is disposed within the inner cup and forms a bearing that rotates within the inner cup. The joint membrane sealed to the inner cup rim and vacuum seals the joint head within the inner cup to form a capsular space. The lubricant is disposed within the capsular space. The implant stem that is attached to a distal bone and that attaches through the joint head through the joint membrane.

7 Claims, 8 Drawing Sheets

MEMBRANE ENCAPSULATED JOINT IMPLANT SEALED UNDER VACUUM

CROSS-REFERENCE TO RELATED APPLICATIONS

This application claims priority to U.S. Provisional Patent Application No. 62/317,910 entitled "MEMBRANCE ENCAPSULATED JOINT SEALED UNDER VACUUM" and filed on Apr. 4, 2016 for Dallin Andrew Hubbard, which is incorporated herein by reference.

FIELD

The present invention relates to artificial biomedical joint implants.

BACKGROUND

Artificial joints assemblies are used when articular joints have become destroyed due to disease or trauma. When motion occurs in artificial joints, the joints grind on each other and create fine wear particles which lead to tissue inflammation and bone loss.

BRIEF SUMMARY

For a membrane encapsulated joint implant sealed under vacuum, a joint implant includes an outer cup, an inner cup, a joint head, a joint membrane, a lubricant, and an implant stem. The outer cup attached at a proximal bone. The nests within the outer cup and receives a joint head, the inner cup comprising an inner cup rim. The joint head is disposed within the inner cup and forms a bearing that rotates within the inner cup. The joint membrane sealed to the inner cup rim and vacuum seals the joint head within the inner cup to form a capsular space. The lubricant is disposed within the capsular space. The implant stem that is attached to a distal bone and that attaches through the joint head through the joint membrane.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

The schematic flowchart diagrams and/or schematic block diagrams in the Figures illustrate the architecture, functionality, and operation of possible implementations. It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Although various arrow types and line types may be employed in the flowchart and/or block diagrams, they are understood not to limit the scope of the corresponding embodiments. Indeed, some arrows or other connectors may be used to indicate only an exemplary logical flow of the depicted embodiment.

The description of elements in each figure may refer to elements of proceeding figures. Like numbers refer to like elements in all figures, including alternate embodiments of like elements.

Figure 1:
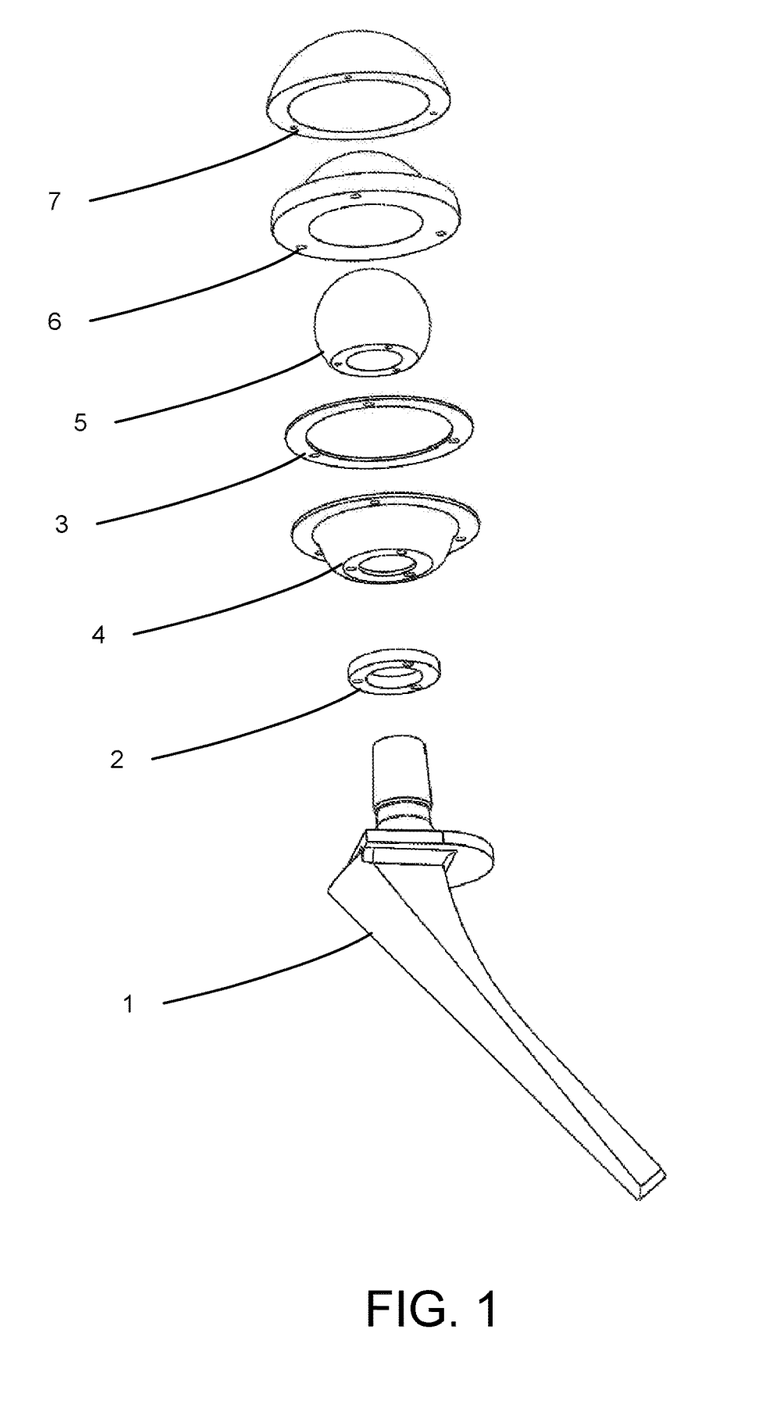
FIG. 1 is an exploded side view diagram illustrating one embodiment of joint implant.

FIG. 1 is an exploded side view diagram illustrating one embodiment of joint implant 10. In the depicted embodiment, the joint implant 10 is a hip joint implant 10. The joint implant 10 may be implanted in a proximal bone selected from the group consisting of an acetabulum bone, a phalangeal bone, a humerus bone, and a spinous process. The joint implant 10 may be selected from the group consisting of a hip implant, a shoulder implant, a phalangeal implant, a spinous implant, and an articular joint. The joint implant 10 includes a plurality of components including an implant stem 1, a joint head O-ring 2, a bone O-ring 3, a joint membrane 4, a joint head 5, an inner cup 6, an outer cup 7. The joint implant 10 may further include a lubricant.

When motion occurs in artificial joints, the joints grind on each other and create fine wear particles which lead to tissue inflammation and bone loss. These wear particles eventually lead to the implant joint loosening or catastrophic bone fractures. These failures must be surgically revised to replace the artificial joint and repair damaged bone. Additionally, the natural wear of the artificial joint components leads to eventual failure of the device even if significant bone loss has not occurred. Significant patient morbidity occurs due to the revision surgeries which could be prevented by a longer lasting design.

Revision surgery in the years after an implant surgery is performed represents a significant morbidity of current joint implants. But dislocation is another problem associated with implants that can occur within a short time frame after joint replacement. Current joint designs are generally non-constrained and thus are easily detached if surrounding muscle and tendons do not provide sufficient compressive force on the joint. Furthermore, current joint implant designs have no resistant to extremes in flexion, extension, abduction and adduction making them susceptible to hyperextension dislocations. These problems again lead to revision surgeries and increased patient morbidity.

The embodiments increase the lifespan of joint implants by encapsulation the joint in vacuum-sealed membrane that prevent particle wear and joint dislocation. This invention may reduce necessary revision surgeries and concomitant patient morbidity.

For example, the joint head 5 may articulate within the inner cup 6. In the past, friction between articulating components of joint implants shed particles from the components. Table 1 shows the particles generated from hip simulator testing of a metal-on-metal hip implant in 95% serum for a 0-0.25 Mc test of Cas, HC-Wrought, and LC-Wrought Alloys.

TABLE 1

|  | Case | HC-Wrought | LC Wrought | Average of Alloys |
|---|---|---|---|---|
| Number of Particles | 1332 | 735 | 1062 | 1043 |
| Round Particles | 227 | 189 | 178 | 227 |
| Oval Particles | 188 | 161 | 266 | 268 |
| Needle-Shaped Particles | 218 | 283 | 219 | 276 |

The particles and metal ions generated from the components may interact with the body and/or enter the bloodstream, harming the patient. For example, the particles and metal ions may cause organ damage and/or bone resorption. As a result, metal-on-metal components have often not been used.

The particles significantly reduce the lifespan of the articulating components, and therefore significantly reduce the lifespan of the joint implant. The shedding of particles is further accelerated as a lubricant cannot be used within the joint implant to reduce friction between articulating components.

The embodiments described herein employ the joint membrane 4 to encapsulate the articulating components. As a result, particles and/or metal ions do not come in contact with tissue and/or blood vessels. As result, the joint implant 10 may employ metal-on-metal articulating components. In one embodiment, the joint membrane 4 maintains a permanent negative pressure. The negative pressure prevents dislocation of components and the migration of particles and metal ions from the joint implant 10.

In addition, the joint membrane 4 and/or negative pressure supports the use of one or more lubricants to reduce the friction of the articulating components. As a result, wear on the articulating components is further reduced, extending the life of the joint implant 10.

Figure 2A:
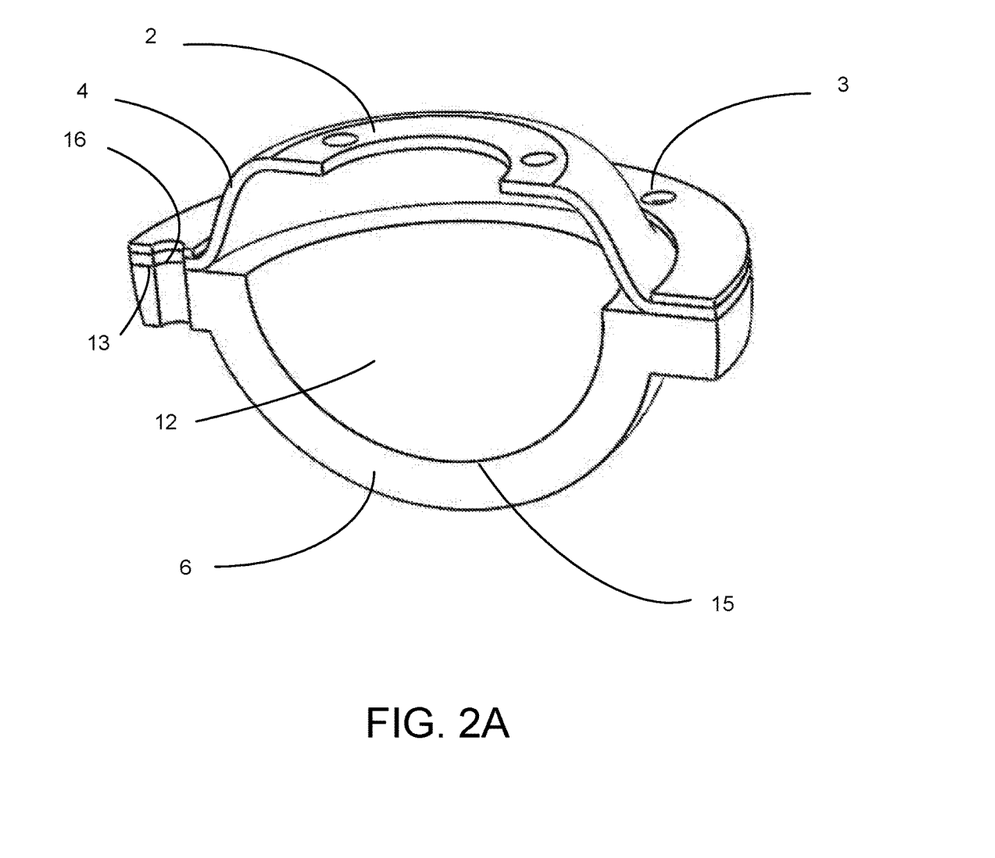
FIG. 2A is a cut away perspective drawing illustrating one embodiment of a capsular space.

FIG. 2A is a cut away perspective drawing illustrating one embodiment of a capsular space 12. For clarity, the joint head 5 is not shown. The capsular space 12 receives the joint head 5. The joint head 5 may articulate within the capsular space 12. The joint head 5 in the inner cup 6 may form a bearing for enhanced articulation of the joint.

The joint membrane 4 may seal the capsular space 12. The joint membrane 4 may be sealed to a rim 13 of the inner cup 6. In one embodiment, the joint membrane 4 is sealed to the rim 13 with a sealant 16. The sealant 16 may be polyurethane.

The joint membrane 4, may be composed of is formed of a material selected from the group consisting of polyurethane, polytetrafluoroethylene (PTFE), Ultra High Molecular Weight Polyethylene, propylene, flexible biocompatible material, and the like. The joint membrane 4 also may include, but is limited to materials previously unemployed in biomedical devices and novel materials.

In the depicted embodiment, the inner cup 6 includes an articular lining 15. The articular lining 15 may separate the inner cup 6 from the joint head 5. An alternative embodiment, the inner cup 6 has no lining.

The outer cup 7, the inner cup 6, the joint head 5, articular lining 15, and the implant stem 1 may each be formed of a material selected from the group consisting of a metal, ceramic, polyethylene, Ultra High Molecular Weight Polyethylene, radiation cross-linked Ultra High Molecular Weight Polyethylene, and the like. These materials may have various surface finishes, such as diamond, oxide, nanoparticles, and microparticles, to enhance the surface characteristics of the implant.

Figure 2B:
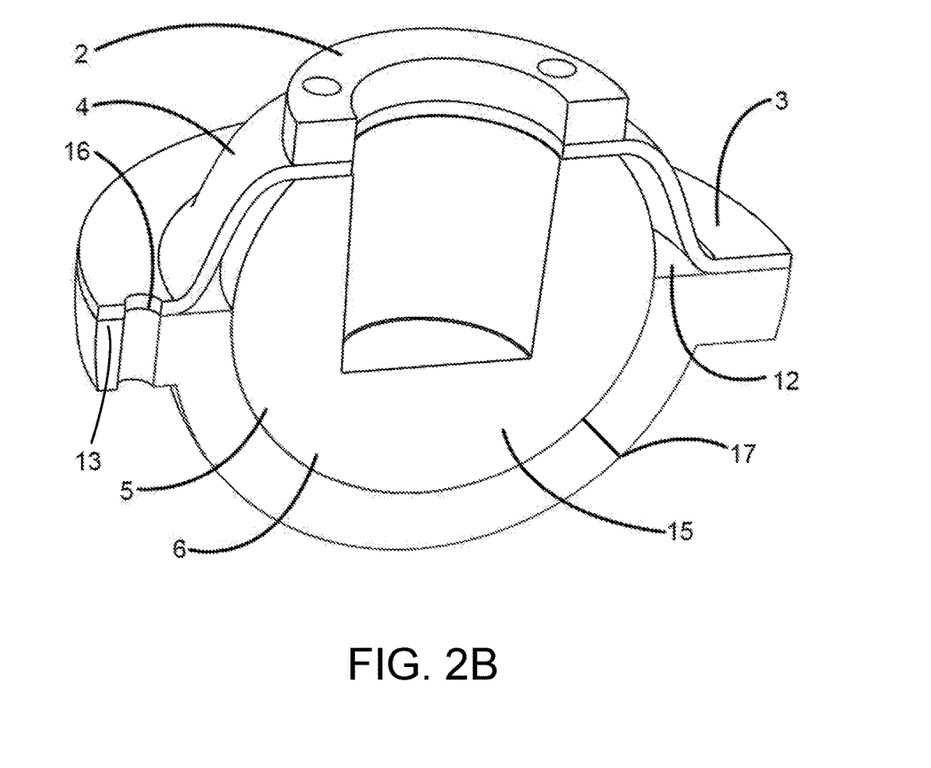
FIG. 2B is a cut away perspective drawing illustrating one embodiment of a capsular space with joint head.

FIG. 2B is a cut away perspective drawing illustrating one embodiment of the capsular space 12 with the joint head 5 disposed within the capsular space 12. In one embodiment, a valve 17 is disposed in the inner cup 6. The valve 17 may be used to evacuate the capsular space 12.

Figure 3A:
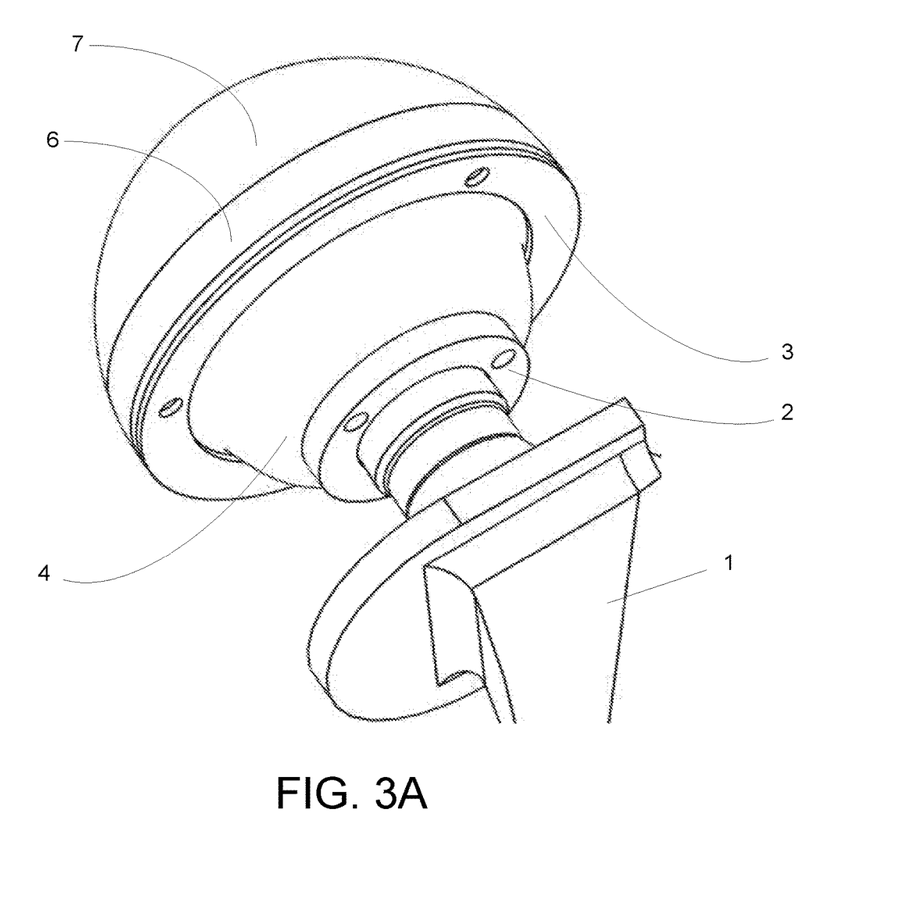
FIG. 3A is a perspective drawing illustrating one embodiment of a joint implant.

FIG. 3A is a perspective drawing illustrating one embodiment of the joint implant 10. The joint head 5 (not shown) is encapsulated in the joint membrane 4. The inner cup 6, joint membrane 6, bone O-ring 3, joint head O-ring 2, and joint head 5 may be preassembled and vacuum-sealed to prevent dislocation of the joint head 5 from the inner cup 6.

The joint head O-ring 2 and the bone O-ring 3 may seal the joint membrane 4 to the joint head 5 and the inner cup 6. The joint head O-ring 2 may be secured to the joint head 5 and/or the joint membrane 4 by one or more fasteners. In addition, the joint head O-ring 2 may be secured to the joint head 5 and/or implant stem 1 with a sealant. The bone O-ring 3 may be secured to the joint head 5 and the inner cup 6 with one or more fasteners.

The joint membrane 4 may capture particles and metal ions that are created by contact of the joint head 5 and the inner cup 6. As a result, the patient is protected from the metal particles and/or metal ions. The negative pressure maintained by the joint membrane 4 may further prevent the dislocation of the joint head 5 from within the inner cup 6. The joint membrane 4 may further retain the lubricant within the capsular space 12.

Figure 3B:
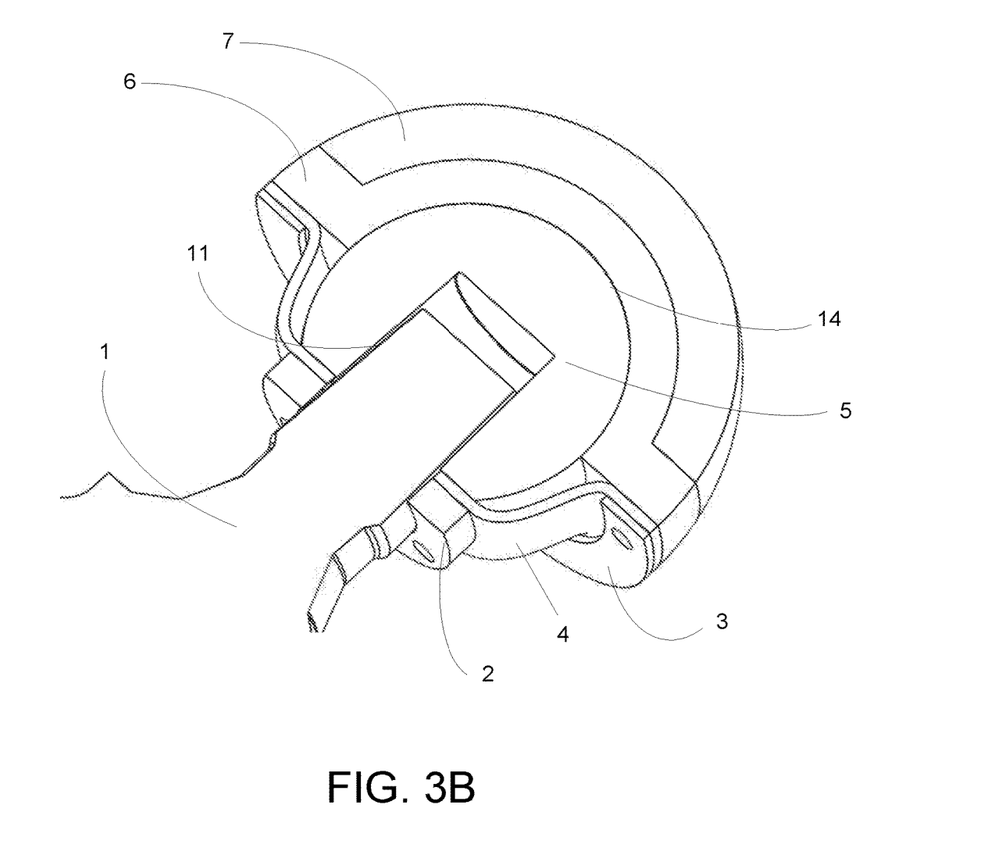
FIG. 3B is a cut away perspective drawing illustrating one embodiment of a joint implant.

FIG. 3B is a cut away perspective drawing illustrating one embodiment of the joint implant 10. The hip joint implant 10 comprises the joint head 5. The joint head may be hemispherical in shape. The joint head 5 articulates in the inner cup 6. The lubricant 14 may be disposed between the joint head 5 and the inner cup 6. The joint head 5 and the inner cup 6 form a bearing. A joint membrane 4 fits over the joint head 5 and the inner cup 6.

The joint membrane 4 may enclose the lubricant 14, which serves to lubricate the joint head 5 and the inner cup 6. The lubricant 14 may comprise one or more of PTFE lubricants or other fluorinated hydrocarbons, silicone lubricants, saline solution, polysaccharide solutions, and petroleum lubricants. In addition, the lubricant 14 may include common oils and solutions used in the mechanical industry including those that are biocompatible and biodegradable, but not limited to such materials. Some common lubricants include natural tissue fluids expressed by the host and secreted into the synovial joint and other inorganic materials may also be used.

The joint head 5 may be attached to an implant stem 1 using a head attachment 11 selected from the group consisting of a morse taper, nut and bolt connection, and threaded attachment. The attachment of the joint head 5 to the implant stem 1 may allow a full range of motion for the joint implant 10.

Figure 4:
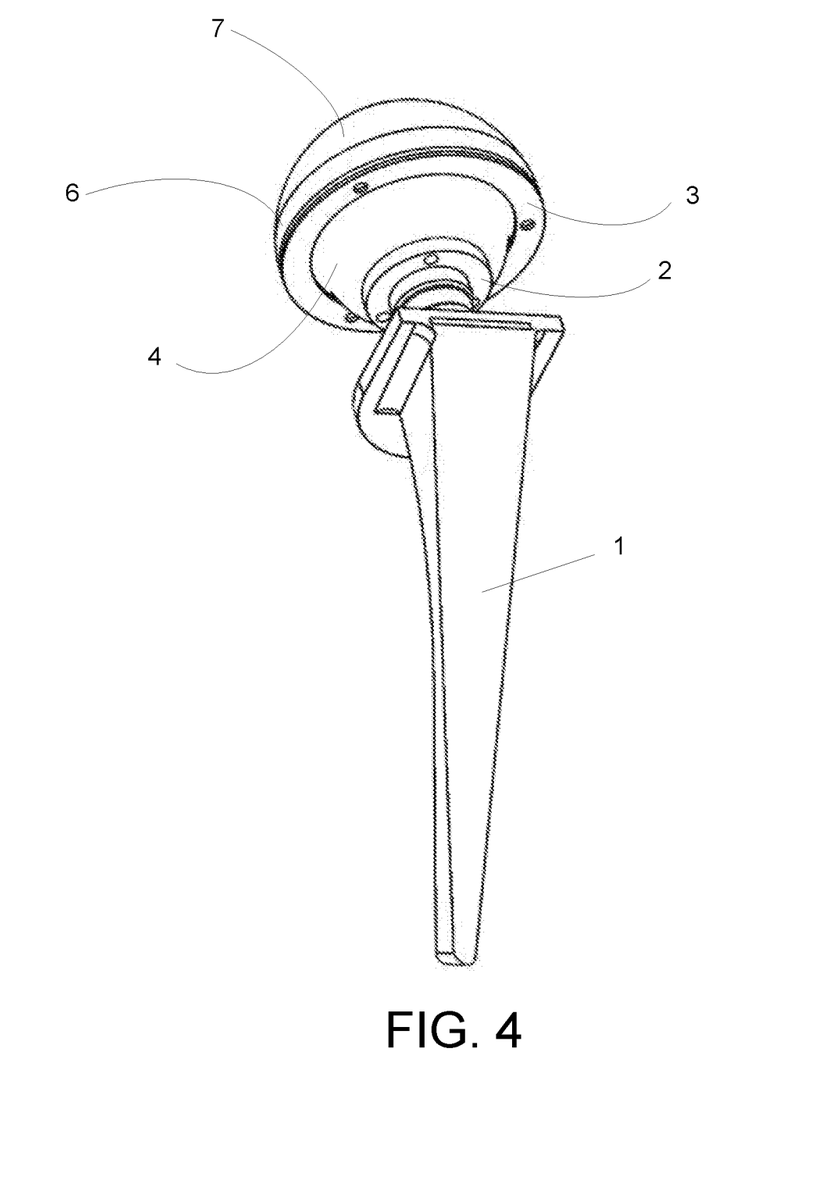
FIG. 4 is a perspective drawing illustrating one embodiment of a joint implant.

FIG. 4 is a perspective drawing illustrating one embodiment of the joint implant 10. The outer cup 7 is attached to the proximal bone (not shown) through bone screws (not shown) or the like. The implant stem 1 is implanted into a distal bone. The implant stem 1 is implanted in a distal bone such as a femur and then fit into the joint head 5 via the head attachment 11 (not shown). The joint head O-ring 2 and the bone O-ring 3 may seal the joint membrane 4 to the joint head 5 and the inner cup 6.

So configured, the joint implant 10 is then ready for full articulation. The embodiments prevent dislocations and the movement of wear particles into the tissue compartment as well as encapsulate a lubricant in the membrane bound space.

Figure 5A:
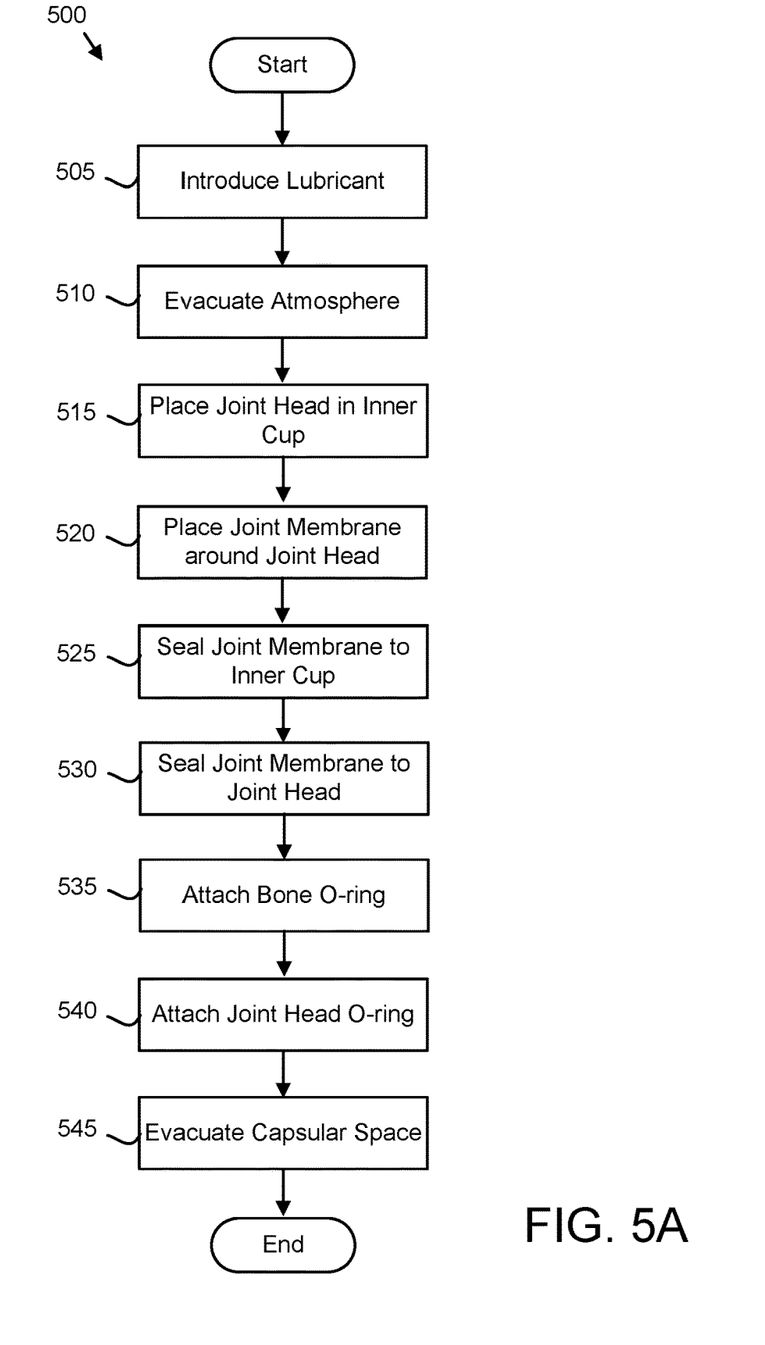
FIG. 5A is a schematic flow chart diagram illustrating one embodiment of a joint implant assembly method.

FIG. 5A is a schematic flow chart diagram illustrating one embodiment of a joint implant assembly method 500. The method 500 may preassembled portions of the joint implant 10.

The method 500 starts, and in one embodiment, the lubricant 14 is introduced 505 into the inner cup 6. The atmosphere may be evacuated 510 around the components. Alternatively, the components may be assembled at atmosphere. In a certain embodiment, an inner gas may be introduced. The joint head 5 is placed 515 in the inner cup 6.

The joint membrane 4 may be placed 520 around the joint head 5 and over the inner cup 6. The joint membrane 4 may be sealed 525 to the inner cup 6. The joint membrane 4 may be sealed 525 with the sealant 16. In addition, the joint membrane 4 may be sealed 530 to the joint head 5.

The bone O-ring 3 may be attached 535 to the inner cup 6 to secure the joint membrane 4 to the inner cup 6 and to seal the capsular space 12. The joint head O-ring 2 may be attached 540 to the joint membrane 4 to seal the joint membrane 4 to seal the capsular space 12.

In one embodiment, the capsular space 12 may be evacuated 545 through the value 17 and the method 500 ends. In a certain embodiment, an inert gas may be added to the capsular space 12 through the value 17.

Figure 5B:
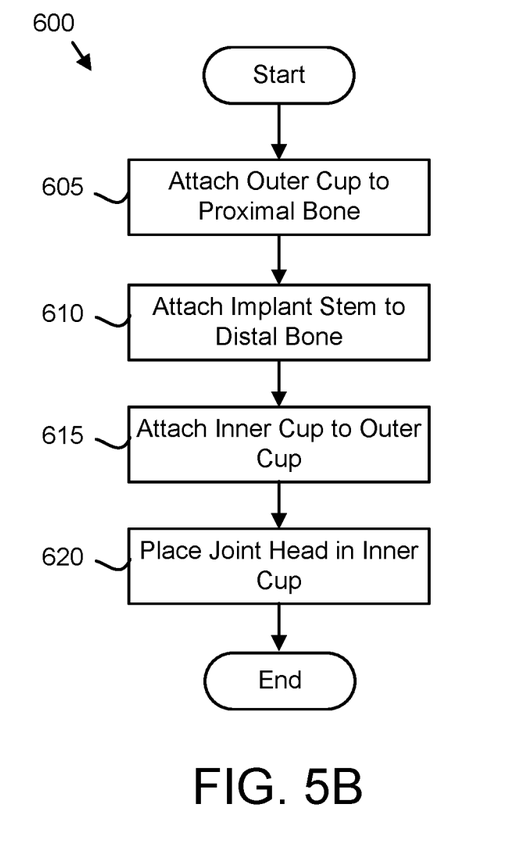
FIG. 5B is a schematic flow chart diagram illustrating one embodiment of a joint implant implantation method.

FIG. 5B is a schematic flow chart diagram illustrating one embodiment of a joint implant implantation method 600. The method 600 may implant the joint implant 10 into a patient. The method 600 starts, and in one embodiment, the outer cup 7 is attached 605 to the proximal bone. The outer cup 7 may be attached 605 with screws, fasteners, or the like.

In addition, the implant stem 1 may be attached 610 to the distal bone. The inner cup 6 and other components may be preassembled. The preassembled components may be attached 615 by the inner cup 6 to the outer cup 7. The implant stem 1 may be attached 620 to the joint head 5 and the method 600 ends. In one embodiment, the implant stem 1 is attached 620 using the head attachment 11.

The depicted joint implant 10 may be a hip joint implant 10, and connect the acetabular bone to the femur bone. Other embodiments of the joint implant 10 include knee joint implants where components are appropriately adjusted to encapsulate an articular implantable knee joint implant 10. In addition, the joint implant 10 may be a shoulder joint implant 10, a finger joint implant 10, and a spinous processes joint implant 10. These embodiments do not represent a limiting itemization of joint implants 10 amenable to the present embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A joint implant comprising:
    an outer cup that is configured to be attached at a proximal bone;
    an inner cup that nests within the outer cup and receives a joint head, the inner cup comprising an inner cup rim;
    a joint head disposed within the inner cup and forms a bearing that rotates within the inner cup;
    a joint membrane sealed to the inner cup rim in a vacuum, wherein the inner cup, the joint membrane, the bone O-ring, the joint head O-ring, and the joint head are preassembled in the vacuum, and that vacuum seals the joint head within the inner cup to form a capsular space;
    a lubricant disposed within the capsular space; and
    an implant stem that is configured to be attached to a distal bone and attaches through the joint head through the joint membrane.

2. The joint implant of claim 1, the joint implant further comprising a bone O-ring that seals the joint membrane to the joint head and the inner cup.

3. The joint implant of claim 1, wherein the joint membrane is formed of a material selected from the group consisting of polyurethane, polytetrafluoroethylene (PTFE), Ultra High Molecular Weight Polyethylene, propylene, and flexible biocompatible material.

4. The joint implant of claim 1, wherein the joint head is attached to the implant stem using a head attachment selected from the group consisting of a morse taper, nut and bolt connection, and threaded attachment.

5. The joint implant of claim 1, wherein the lubricant comprises one or more of PTFE lubricants or other fluorinated hydrocarbons, silicone lubricants, saline solution, polysaccharide solutions, and petroleum lubricants.

6. The joint implant of claim 1, wherein the outer cup, the inner cup, the joint head and the implant stem are each formed of a material selected from the group consisting of a metal, ceramic, polyethylene, Ultra High Molecular Weight Polyethylene, and radiation cross-linked Ultra High Molecular Weight Polyethylene.

7. The joint implant of claim 1, wherein the inner cup has no lining.

* * * * *